US008815253B2

(12) United States Patent
Malyala et al.

(10) Patent No.: US 8,815,253 B2
(45) Date of Patent: Aug. 26, 2014

(54) COMPOSITIONS FOR INDUCING IMMUNE RESPONSES (75) Inventors: Padma Malyala, Santa Clara, CA (US); Derek O'Hagan, Winchester, MA (US); Manmohan Singh, Lexington, MA (US)

(73) Assignee: Novartis AG, Basel (CH)

( * ) Notice: Subject to any disclaimer, the term of this patent is extended or adjusted under 35 U.S.C. 154(b) by 765 days.

(21) Appl. No.: 12/746,723

(22) PCT Filed: Dec. 4, 2008

(86) PCT No.: PCT/US2008/085506
§ 371 (c)(1),
(2), (4) Date: Sep. 21, 2010

(87) PCT Pub. No.: WO2009/076158
PCT Pub. Date: Jun. 18, 2009

(65) Prior Publication Data
US 2011/0135679 A1    Jun. 9, 2011

Related U.S. Application Data (60) Provisional application No. 61/005,704, filed on Dec. 7, 2007.

(51) Int. Cl.
| A61K 39/02 | (2006.01) |
| A61K 49/00 | (2006.01) |
| A61K 39/00 | (2006.01) |
| A61K 31/437 | (2006.01) |
| A61K 9/16 | (2006.01) |
| A61K 39/07 | (2006.01) |
| A61K 31/4745 | (2006.01) |
| A61K 39/39 | (2006.01) |

(52) U.S. Cl.
CPC ............. *A61K 31/437* (2013.01); *A61K 9/1647* (2013.01); *A61K 2039/57* (2013.01); *A61K 2039/55511* (2013.01); *A61K 39/07* (2013.01); *A61K 31/4745* (2013.01); *A61K 39/39* (2013.01)
USPC ........ 424/234.1; 424/9.1; 424/9.2; 424/184.1; 424/400; 424/489; 424/490; 424/499; 424/204.1

(58) Field of Classification Search
USPC ........ 424/9.1, 9.2, 184.1, 400, 489, 490, 499, 424/204.1, 234.1
See application file for complete search history.

(56) References Cited

U.S. PATENT DOCUMENTS

| 5,389,640 | A | 2/1995 | Gerster et al. |
| 6,086,901 | A | 7/2000 | O'Hagan et al. |
| 6,146,632 | A | 11/2000 | Momin et al. |
| 6,299,884 | B1 | 10/2001 | Van Nest et al. |
| 6,451,325 | B1 | 9/2002 | Van Nest et al. |
| 6,534,064 | B1 | 3/2003 | O'Hagan et al. |
| 7,501,134 | B2 | 3/2009 | O'Hagan et al. |
| 7,731,967 | B2 | 6/2010 | O'Hagan et al. |
| 2003/0139364 | A1 | 7/2003 | Krieg et al. |
| 2004/0202669 | A1 | 10/2004 | O'Hagan |
| 2005/0107322 | A1 | 5/2005 | O'Hagan et al. |
| 2005/0118275 | A1 | 6/2005 | O'Hagan |
| 2005/0220883 | A1 | 10/2005 | O'Hagan et al. |
| 2006/0088542 | A1 | 4/2006 | Braun |
| 2010/0239607 | A1 | 9/2010 | O'Hagan et al. |

FOREIGN PATENT DOCUMENTS

| EP | 0142193 | | 5/1998 |
| WO | 95/11008 | A2 | 4/1995 |
| WO | 98/33487 | | 8/1998 |
| WO | 98/50071 | | 11/1998 |
| WO | 99/22763 | A2 | 5/1999 |
| WO | 00/06123 | | 2/2000 |
| WO | 0006123 | | 2/2000 |
| WO | 0050006 | | 8/2000 |
| WO | 01/26681 | | 4/2001 |
| WO | 02/24225 | | 3/2002 |
| WO | 03/028661 | | 1/2003 |
| WO | 03/028656 | | 4/2003 |
| WO | 2003/059252 | A2 | 7/2003 |
| WO | 03/070909 | | 8/2003 |
| WO | 03070909 | | 8/2003 |
| WO | 03/077944 | | 9/2003 |
| WO | 03/080114 | | 10/2003 |
| WO | 03/094836 | | 11/2003 |
| WO | 2004098509 | | 11/2004 |
| WO | 2006031878 | | 3/2006 |
| WO | WO2006/031878 | * | 3/2006 |
| WO | 2007013893 | | 2/2007 |
| WO | 2007052058 | | 5/2007 |
| WO | 2007100699 | | 9/2007 |
| WO | 2007109810 | | 9/2007 |

OTHER PUBLICATIONS

Tomai, et al, "Resiquimod and other immune response modifiers as vaccine adjuvants" Expert Review of Vaccines, Oct. 2007. vol. 6, No. 5., pp. 835-847.
Singh, M. et al. "A preliminary evaluation of alternative adjuvants to alum using a range of established and new generation vaccine antigens." Vaccine, Mar. 6, 2006;24(10), pp. 1680-1686.
Kensil et al., "Current vaccine adjuvants: an overview of a diverse class," Frontiers in Bioscience (2004) 9:2972-2988.
Vasilakos et al., "Adjuvant activities of immune response modifier R-848. Comparison with CpG ODN," Cellular Immunology (2000) 204: 64-741.
A. Spickler et al "Adjuvants in Veterinary Vaccines: Modes of Action and Adverse Effects", J Vet Intern Med 2003; 17:273-281.
J.Cox et al., "Adjuvants-A Classificaton and Review of Their Modes of Action" Vaccine. vol. 15 No. 3, pp. 248-256, 1997.

(Continued)

*Primary Examiner* — Rodney P Swartz
(74) *Attorney, Agent, or Firm* — Helen Lee; David Bonham (57) ABSTRACT

The invention provides, inter alia, immunogenic compositions that comprise (a) a first antigen, (b) at least first and second adjuvants, wherein the first adjuvant comprises microparticles and wherein the second adjuvant comprises an imidazoquinoline compound, and (c) a pharmaceutically acceptable excipient, which compositions elicits an immune response when administered to a vertebrate subject. The invention also provides methods of producing immunogenic compositions and methods for using immunogenic compositions (e.g., for treatment), among other benefits.

57 Claims, 1 Drawing Sheet

(56) References Cited

OTHER PUBLICATIONS

N. Burdin et al., "Immunological Foundations to the Quest for New Vaccine Adiuvants"., Biodrugs 2004; 18(2): 79-93.

Menyhart, Lisa, Lyophilization: Freeze-Drying A Downstream Process, Dec. 6, 1995, three pages; available from http://www.rpi.edu/dept/chem-eng/Biotech-Environ/LYO/.

Wang et al., International Journal of Pharmaceutics, 1998, 166:1-14.

K.F. Griffin et al., "Immune Responses to V Antigen of *Yersinia Pests* Co-Encapsulated with IFN-y: Effect of Dose and Formulation", Vaccine, vol. 16, No. 5, Mar. 1998, pp. 517-521.

U.R. Hengge et al., "Tropical Immunomodulators-Progress Towards Treating Inflammation Infection, and Cancer", Lancet Infectious Diseases, vol. 1. No. 3, Oct. 2001, pp. 189-198.

Francesca Brugnolo et al., "The Novel synthetic Immune Response Modifier R-848 (Resiquimod) Shints Human Allergen-Specific CD4+TH2 Lymphoncytes into IFN-y-PRoducing Cells", Journal of Allergy and clinical Immunology, vol. 11, No. 2, Feb. 2003, pp. 380-388.

D.H. Dockrell, et al., "Imiquimod and Resiquimod as Novel Immunomodulators", Journal of Anitmicrobial Chemotherapy, vol. 48, No. 6, Dec. 2001, pp. 751-755.

K.D. Newman et al., "Ovalbumin Peptide Encapsulated in Poly(d,I lactic-co-glycolic acid) Microspheres in Capable of inducing a T Helper Type 1 Immune Response", Journal of Controlled Release, vol. 54, No. 1, Jun. 1998, pp. 49-59.

P. Johansen et al., "Revisiting PLA/PLGA Microspheres: An analysis of Their Potential in Parenteral Vaccination", European Journal of Pharmaceuticals and Biopharmaceutices, vol. 50, No. 1, Jul. 3, 2000, pp. 129-146.

Imbertson et al., "Antiviral and Immunomodulating Activities of the Imidazoquinoline S-28463", Antiviral Research 26: A301, Mar. 1995.

St. Clair, N. et al., "Cross-Linked Protein Crystals for Vaccine Delivery", Applied Viol. Sci., 98:9489-9474, 1999.

R. Edelman, "The Development and Use of Vaccine Adjuvants", Molecular Biotechnology, vol. 21, 2002, pp. 129-148.

\* cited by examiner

Fig. 1

COMPOSITIONS FOR INDUCING IMMUNE RESPONSES

The present application is a 371 National Phase Application of PCT/US2008/085506 filed Dec. 4, 2008, the disclosure of which is hereby incorporated by reference in its entirety, and which claims the benefit of U.S. Provisional Application 61/005,704, filed Dec. 7, 2007, the disclosure of which is hereby incorporated by reference in its entirety.

FIELD OF THE INVENTION

The present invention relates generally to immunogenic compositions and to agents that enhance the immune response to one or more selected antigens.

BACKGROUND OF THE INVENTION

The emergence of subunit vaccines created by recombinant DNA technology has intensified the need for safe and effective adjuvant-containing compositions. Subunit vaccines, while offering significant advantages over traditional live and killed vaccines in terms of safety and cost of production, generally present isolated polypeptides or mixtures of isolated polypeptides to the immune system, which have limited immunogenicity as compared to, for example, whole viruses, bacteria and other microorganisms. As a result, these vaccines generally benefit from adjuvants with immunostimulatory capabilities, which help them to reach their full potential in treating disease.

Traditional live vaccines, on the other hand, commonly do not require adjuvants. Moreover, killed vaccines are generally more immunogenic than subunit vaccines and commonly do not require adjuvants. Nonetheless, these vaccines, like subunit vaccines, can also benefit from adjuvants with immunostimulatory capabilities.

SUMMARY OF THE INVENTION

The present invention provides immunogenic compositions that comprise (a) a first antigen, (b) at least first and second adjuvants, wherein the first adjuvant comprises microparticles and wherein the second adjuvant comprises an imidazoquinoline compound, and (c) a pharmaceutically acceptable excipient, which compositions elicits an immune response when administered to a vertebrate subject.

In some embodiments, the present invention provides pharmaceutical compositions comprising immunogenic compositions of the present invention.

In some embodiments, the present invention provides injectable vaccine compositions comprising immunogenic compositions in accordance with the present invention.

In some embodiments, the present invention provides kits for preparing an immunogenic composition comprising a first container comprising an antigen, a second container comprising an imidazoquinoline compound, and a third container comprising microparticles, or a first container comprising an antigen and a second container comprising an imidazoquinoline compound and microparticles.

In some embodiments, the present invention provides methods for eliciting immune responses in a vertebrate subject comprising administering to the vertebrate subject an effective amount of an immunogenic composition in accordance with the present invention.

In some embodiments, the present invention provides methods for eliciting a cytotoxic-T lymphocyte (CTL) response in a vertebrate subject comprising administering to the vertebrate subject an effective amount of an immunogenic composition of the present invention.

In some embodiments, the present invention provides methods of eliciting an antibody-mediated immune response in a vertebrate subject individual comprising administering an effective amount of an immunogenic composition of the present invention to the vertebrate subject.

In some embodiments, the present invention provides methods of making immunogenic compositions such as those described herein.

These and other embodiments of the present invention will readily occur to those of ordinary skill in the art in view of the disclosure herein.

DETAILED DESCRIPTION OF THE INVENTION

The practice of the present invention will employ, unless otherwise indicated, conventional methods of virology, chemistry, biochemistry, recombinant technology, immunology and pharmacology, within the skill of the art. Such techniques are explained fully in the literature. See, e.g., Virology, 3rd Edition, vol. I & II (B. N. Fields and D. M. Knipe, eds., 1996); Remington's Pharmaceutical Sciences, 18th Edition (Easton, Pa.: Mack Publishing Company, 1990); Methods In Enzymology (S. Colowick and N. Kaplan, eds., Academic Press, Inc.); Handbook of Experimental Immunology, Vols. I-IV (D. M. Weir and C. C. Blackwell, eds., 1986, Blackwell Scientific Publications); Sambrook et al., Molecular Cloning: A Laboratory Manual (2nd Edition, 1989); and DNA Cloning: A Practical Approach, vol. I & II (D. Glover, ed.).

A. Definitions

As used herein, the singular forms "a," "an" and "the" include plural references unless the content clearly dictates otherwise.

As used herein, the term "about" refers to +/−10% of a value.

As used herein, the phrase "injectable composition," or variants thereof, refers to pharmaceutically acceptable compositions suitable for injection into a vertebrate subject, which compositions are typically sterile, pyrogen-free, and possess specific pH and isotonicity values suitable for injection.

By "pharmaceutically acceptable" or "pharmacologically acceptable" is meant a material which is not biologically or otherwise undesirable, e.g., the material may be administered to an individual without causing any undesirable biological effects or interacting in a deleterious manner with any of the components of the composition in which it is contained.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

By "physiological pH" or a "pH in the physiological range" is meant a pH in the range of approximately 7.2 to 8.0 inclusive, more typically in the range of approximately 7.2 to 7.6 inclusive.

As used herein, "treatment" refers to any of (i) the prevention of a condition (e.g., a disease or disorder) in question (e.g. cancer or a pathogenic infection, as in a traditional vaccine), (ii) the reduction or elimination of symptoms associated with the condition in question, and (iii) the substantial or complete elimination of the condition in question. Treatment may be effected prophylactically (prior to arrival of the condition in question) or therapeutically (following arrival of the same).

The terms "effective amount" or "pharmaceutically effective amount" of an immunogenic composition of the present invention refer herein to a sufficient amount of the immunogenic composition for the treatment or diagnosis of a condition of interest. The exact amount required will vary from subject to subject, depending, for example, on the species, age, and general condition of the subject; the severity of the condition being treated; the particular antigen of interest; in the case of an immunological response, the capacity of the subject's immune system to synthesize antibodies, for example, and the degree of protection desired; and the mode of administration, among other factors. An appropriate "effective" amount in any individual case may be determined by one of ordinary skill in the art. Thus, a "therapeutically effective amount" will typically fall in a relatively broad range that can be determined through routine trials.

As used herein, the term "microparticle" refers to a particle of about 10 nm or less to about 150 µm in diameter, for example, ranging from 10 nm to 25 nm to 50 nm to 100 nm to 250 nm to 500 nm to 1 µm to 2.5 µm to 5 µm to 10 µm to 25 µm to 50 µm to 100 µm to 150 µm. In some embodiments, the microparticles described herein can be generally spherical. In some embodiments, the microparticles described herein can be of irregular geometry.

As used herein, the term "protein particle" refers to a particle that comprises at least 50 wt % protein, a "polysaccharide particle" refers to a particle that comprises at least 50 wt % polysaccharide, and so forth.

Microparticles may aggregate into larger masses under some circumstances. As a specific example, microparticles having adsorbed DNA may be, for instance, about 0.5-2 µm in diameter pre-lyophilization, while the same particles may be, for instance, in aggregates having a diameter of about 5-15 µm post-lyophilization. The microparticle will generally be of a diameter that permits parenteral or mucosal administration without occluding needles and capillaries. Microparticle size is readily determined by techniques well known in the art, such as photon correlation spectroscopy, laser diffractometry and/or scanning electron microscopy. The term "particle" may also be used to denote a microparticle as defined herein.

The term "polypeptide" refers to a polymer of amino acid residues and is not limited to a minimum length of the product. Thus, full length proteins, peptides, oligopeptides, dimers, multimers, and the like, are included within the definition.

A "polypeptide-containing species" is a molecule, at least a portion of which is a polypeptide. Examples include polypeptides, proteins including glycoproteins, metalloproteins and lipoproteins, polysaccharide antigens conjugated to carrier proteins, and so forth. Proteins for use herein include full-length proteins and fragments thereof. In certain embodiments, modifications to the native sequence, such as deletions, additions and substitutions (generally conservative in nature), are employed.

The term "fragment" as used herein refers to a physically contiguous portion of the primary structure of a biomolecule. In the case of proteins, a fragment may be defined by a contiguous portion of the amino acid sequence of that protein and may be at least 3-5 amino acids, at least 6-10 amino acids, at least 11-15 amino acids, at least 16-24 amino acids, at least 25-30 amino acids, and at least 30-45 amino acids. In the case of polynucleotide, a fragment is defined by a contiguous portion of the nucleic acid sequence of that polynucleotide and may be at least 9-15 nucleotides, at least 15-30 nucleotides, at least 31-45 nucleotides, at least 46-74 nucleotides, at least 75-90 nucleotides, and at least 90-130 nucleotides. In some embodiments, fragments of biomolecules are immunogenic fragments.

In some embodiments, the antigen is a protein particle. Protein particles may have the following physical characteristics. The protein particles are generally spherical in shape and generally possess a diameter of about 150 nm about 200 nm to about 500 nm to about 1 µm to about 2 µm to about 5 µm to about 10 µm in diameter. Protein particles may be formed as described in U.S. Pat. No. 6,534,064 to O'Hagan et al. or Pub. No. US 2005/0107322 to O'Hagan et al.

A "polynucleotide" is a nucleic acid polymer. A polynucleotide can include as few as 5, 6, 7 or 8 nucleotides. Furthermore, a "polynucleotide" can include both double- and single-stranded sequences and refers to, but is not limited to, cDNA from viral, procaryotic or eukaryotic mRNA, genomic RNA and DNA sequences from viral (e.g. RNA and DNA viruses and retroviruses), prokaryotic or eukaryotic organisms, and synthetic DNA sequences. The term also captures sequences that include any of the known base analogs of DNA and RNA. The term further includes modifications, such as deletions, additions and substitutions (generally conservative in nature), to a native sequence, for example, where the nucleic acid molecule encodes an antigenic protein. These modifications may be deliberate, as through site-directed mutagenesis, or may be accidental, such as through mutations of hosts that produce antigens.

A "polynucleotide-containing species" is a molecule, at least a portion of which is a polynucleotide. Examples include RNA vector constructs, DNA vector constructs and so forth.

As used herein the term "saccharide" encompasses monosaccharides, oligosaccharides and polysaccharides. A "saccharide-containing species" is a molecule, at least a portion of which is a saccharide. Examples include saccharide antigens, antigens comprising saccharides conjugated to carrier peptides, and so forth.

As used herein the term "isolated" refers to a chemical species such as a polynucleotide, a polypeptide, and an antibody, etc. that is in an environment different from that in which the chemical species naturally occurs. A chemical species which is isolated is generally substantially purified. Methods of isolating cells are also well known to those skilled in the art.

A "purified" protein is a protein which is produced (e.g., recombinantly or synthetically) or isolated from its natural host, such that the amount of protein present in a composition is substantially higher than that present in a crude preparation. In general, a purified protein will be at least about 50% homogeneous, more preferably at least about 80%, about 85%, about 90%, about 95%, about 97%, about 98%, about 99%, or more, homogeneous.

As used herein, an "immunological response" to an antigen or composition is the development in a subject of a humoral and/or a cellular immune response to the antigen or composition. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL's"). CTLs have specificity for peptide antigens that are presented in association with proteins encoded by the MHC and expressed on the surfaces of cells. CTLs help induce and promote the intracellular destruction of intracellular microbes, or the lysis of cells infected with such microbes. Another aspect of cellular immunity involves an antigen-specific response by helper T-cells which act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

An "antigen" refers to a molecule containing one or more epitopes (either linear, conformational or both) that elicit an immunological response. The term may be used interchangeably with the term "immunogen." An "epitope" is that portion of given species (e.g., an antigenic molecule or antigenic complex) that determines its immunological specificity. An epitope is within the scope of the present definition of antigen. Commonly, an epitope is a polypeptide or polysaccharide in a naturally occurring antigen. In artificial antigens it can be a low molecular weight substance such as an arsanilic acid derivative. Normally, a B-cell epitope will include at least about 5 amino acids but can be as small as 3-4 amino acids. A T-cell epitope, such as a CTL epitope, will typically include at least about 7-9 amino acids, and a helper T-cell epitope will typically include at least about 12-20 amino acids. The term "antigen" denotes both subunit antigens, i.e., antigens which are separate and discrete from a whole organism or cell with which the antigen is associated in nature, as well as killed, attenuated or inactivated bacteria, viruses, fungi, parasites or other microbes or tumor cells. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

Thus, for purposes of the present invention, antigens can be derived from any of the various viruses, bacteria, parasites, fungi and other microbes, as well as any of the various tumor antigens. Antigens also include nucleic acids which express an antigen or antigenic determinant in vivo. As a few specific examples, antigens may be proteins from or derived from the herpes virus family, including proteins derived from herpes simplex virus (HSV) types 1 and 2, such as HSV-1 and HSV-2 glycoproteins gB, gD and gH; proteins derived from cytomegalovirus (CMV) including CMV gB and gH; proteins derived from hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV); proteins, including gp120, gp160, gp41, p24gag and p55gag envelope proteins, derived from HIV, including members of the various genetic subtypes of HIV isolates $HIV_{IIIb}$, $HIV_{SF2}$, $HIV_{LAV}$, $HIV_{LAI}$, $HIV_{MN}$, $HIV-1_{CM235}$, $HIV-1_{US4}$, HIV-2; proteins derived from simian immunodeficiency virus (SIV); and proteins derived from *Neisseria meningitidis* (A, B, C, Y), *Hemophilus influenza* type B (HIB), *Helicobacter pylori*; human serum albumin and ovalbumin, among many others.

An immunogenic composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host. The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., J. Immunol. (1993) 151:4189-4199; Doe et al., Eur. J. Immunol. (1994) 24:2369-2376. Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by, e.g., but not limited to B-cells; and/or the activation of suppressor T-cells and/or γΔ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An immunogenic composition which contains an antigen in accordance with the present invention displays "enhanced immunogenicity" when it possesses a greater capacity to elicit an immune response than the immune response elicited by an equivalent amount of the antigen administered using a different delivery system, e.g., wherein the antigen is administered as a soluble protein. Thus, an immunogenic or vaccine composition may display "enhanced immunogenicity" because the antigen is more strongly immunogenic or because a lower dose or fewer doses of antigen are necessary to achieve an immune response in the subject to which the antigen is administered. Such enhanced immunogenicity can be determined by administering the antigen composition and antigen controls to animals and comparing antibody titers and/or cellular-mediated immunity against the two using standard assays described herein.

The term "adjuvant" refers to any substance that assists or modifies the action of an antigen in the immune system. Adjuvants can potentiate humoral and/or cellular immunity.

The term "excipient" refers to any essentially accessory substance that may be present in the finished dosage form. For example, the term "excipient" includes vehicles, binders, disintegrants, fillers (diluents), suspending/dispersing agents, and so forth.

As used herein, the phrase "vector construct" generally refers to any assembly that is capable of directing the expression of a nucleic acid sequence(s) or gene(s) of interest. A "DNA vector construct" refers to a DNA molecule that is capable of directing the expression of a nucleic acid sequence(s) or gene(s) of interest. One specific type of DNA vector construct is a plasmid, which is a circular episomal DNA molecule capable of autonomous replication within a host cell. Typically, a plasmid is a circular double stranded DNA loop into which additional DNA segments can be ligated. pCMV is one specific plasmid that is well known in the art. Other DNA vector constructs are known, which are based on RNA viruses. These DNA vector constructs typically comprise a promoter that functions in a eukaryotic cell, 5' of a cDNA sequence for which the transcription product is an RNA vector construct (e.g., an alphavirus RNA vector replicon), and a 3' termination region. Other examples of vector constructs include RNA vector constructs (e.g., alphavirus vector constructs) and the like. As used herein, "RNA vector construct", "RNA vector replicon" and "replicon" refer to an RNA molecule that is capable of directing its own amplification or self-replication in vivo, typically within a target cell. The RNA vector construct is used directly, without the requirement for introduction of DNA into a cell and transport to the nucleus where transcription would occur. By using the RNA vector for direct delivery into the cytoplasm of the host cell, autonomous replication and translation of the heterologous nucleic acid sequence occurs efficiently.

B. General

The present invention provides immunogenic compositions comprising (a) a first antigen, (b) at least first and second adjuvants, wherein the first adjuvant comprises a microparticle and wherein the second adjuvant comprises an imidazoquinoline, and (c) a pharmaceutically acceptable excipient, wherein said composition elicits an immune response when administered to a vertebrate subject.

In some embodiments, the first antigen is a killed or live (e.g., attenuated or inactivated) pathogenic organism. In some embodiments, the first antigen is a polypeptide-containing antigen (e.g., full-length proteins, protein fragments, etc.). In some embodiments, the first antigen is a polysaccharide-containing antigen (e.g., a capsular polysaccharide, a polysaccharide-protein protein conjugate, etc.). In some embodiments, the first antigen is a polynucleotide-containing antigen (e.g., a polynucleotide that is linked to a regulatory sequence which controls expression of the polynucleotide, etc.). In some embodiments the first antigen is form of a stabilized microparticle that is formed from an antigen such as one of the preceding, which microparticle may be produced, for example, as described in U.S. Pat. No. 6,534,064 or Pub. No. US 2005/0107322 to O'Hagan et al. or by other means known to those of skill in the art. While such stabilized microparticles are not virus-like particles, in some embodiments, the first antigen is a virus-like particle. Such stabilized microparticles are typically free particles and are not entrapped within a carrier.

Immunogenic compositions in accordance with the invention can also be used in methods for eliciting an immune response, for example, a cytotoxic-T lymphocyte (CTL) response, an antibody-mediated immune response, or both, in a vertebrate subject, which comprise administering to the vertebrate subject the immunogenic composition.

In some embodiments, the immunogenic compositions of the invention are used in an injectable vaccine to treat, for example, a pathogen or tumor.

Immunogenic compositions in accordance with the invention can also be prepared as pharmaceutical compositions.

The present invention also provides kits for preparing immunogenic compositions. The kits may comprise, for example, a first container comprising an antigen and a second container comprising microparticles and an imidazoquinoline. The kits also may comprise, for example, a first container comprising an antigen, a second container comprising microparticles, and a third container comprising an imidazoquinoline.

In some embodiments, the immunogenic compositions of the invention can further comprise at least a third adjuvant, and in some cases may comprise 3, 4, 5 or more adjuvants.

In some embodiments, the compositions further comprise a second antigen. Like the first antigen, the second antigen may be, for example, a killed or live pathogenic organism, a polypeptide-containing antigen, a polysaccharide-containing antigen, a polynucleotide-containing antigen, a stabilized microparticle, and so forth. In some embodiments, the immunogenic compositions of the invention can further comprise 2, 3, 4 or more antigens.

C. Imidazoquinolines

Preferred imidazoquinolines are those of the formula, where $R_1$ and $R_2$ are independently selected from the group consisting of hydrogen, alkyl of one to ten carbon atoms, hydroxyalkyl of one to ten carbon atoms, alkoxyalkyl of one to ten carbon atoms, acyloxyalkyl wherein the acyloxy moiety is alkanoyloxy of one to five carbon atoms or benzoyloxy and wherein the alkyl moiety contains one to six carbon atoms, wherein $R_3$ and $R_4$ are independently selected from the group consisting of hydrogen and alkyl of one to ten carbon atoms, benzyl, (phenyl)ethyl and phenyl, where the benzyl, (phenyl)ethyl or phenyl substituent are optionally substituted on the benzene ring by one or two moieties independently selected from the group consisting of alkyl of one to four carbon atoms, alkoxy of one to four carbon atoms and halogen. The preceding alkyl groups may be linear, branched and/or cyclic. Particularly preferred imidazoquinolines for the practice of the present invention include imiquimod, resiquimod, and the latter of which is also referred to herein as "imidazoquinoline 090". See, e.g., Int. Pub. Nos. WO 2006/031878 to Valiante et al. and WO 2007/109810 to Sutton et al.

Typical wt/wt ratios of antigen to imidazoquinoline in the compositions of the present invention range from 1:1 to 2:1 to 5:1 to 10:1, among other possibilities.

D. Microparticles

As indicated above, in addition to one or more antigens and one or more imidazoquinolines, compositions in accordance with certain embodiments comprise one or more types of microparticles. Examples of microparticles include (a) inorganic microparticles (e.g., microparticles comprising calcium phosphate, microparticles comprising aluminum salts [alum], such as aluminum hydroxide, aluminum phosphate, aluminum sulfate, etc.) and (b) organic microparticles such as those based on low solubility amino acids (e.g., L-tyrosine microparticles, etc.), biodegradable polymers (e.g., PLG, etc.), metabolizable oils (e.g., MF59, etc.), and so forth.

Where the microparticles are solid microparticles, the antigen(s), imidazoquinoline(s), and various optional supplementary components may independently be, for example: (a) established within the microparticles, (b) attached to the microparticles, for example, adsorbed or conjugated to the surface of the microparticles, and/or (c) otherwise associated with the microparticles to varying degrees, for example, admixed with the microparticles in a liquid dispersion, admixed with the microparticles in a solid composition (e.g., colyophilized with the microparticles), and so forth. The antigen(s), imidazoquinoline(s) and various optional supplementary components may be adsorbed to, conjugated to or established within separate populations of microparticles.

Where the microparticles are liquid microparticles (e.g., oil droplets in an oil-in-water emulsion, etc.), the antigen(s), imidazoquinoline(s) and various supplementary components may independently be, for example: dissolved or dispersed within the oil phase(s) of the emulsion (including separate populations of oil droplets), dissolved or dispersed within the aqueous phase of the emulsion and/or disposed at the interfaces between aqueous and oil phases of the emulsion.

The antigen(s), imidazoquinoline(s) or various supplementary components may be established within the microparticles (e.g., entrapped, encapsulated, dissolved or dispersed in the microparticles), for example, by introducing these species during the microparticle manufacturing process. The antigen(s), imidazoquinoline(s) or various supplementary components may be attached to the microparticles, adsorbed to the microparticles, or otherwise associated with the microparticles, for example, by introducing these species to previously formed microparticles.

Typical wt/wt ratios of antigen to microparticles range from 100:1 to 200:1 to 500:1 to 1000:1, among other possibilities.

In some embodiments, the microparticles comprise one or more inorganic species (e.g., microparticles comprising calcium phosphate, microparticles comprising aluminum salts [alum], such as aluminum hydroxide, aluminum phosphate, aluminum sulfate, etc.). For example, aluminum hydroxide and calcium phosphate may be obtained from Brenntag Biosector, Denmark, among other sources.

In some embodiments, the microparticles comprise one or more low solubility amino acids (e.g., L-tyrosine microparticles, etc.). L-tyrosine microparticle suspensions are described, for example, in M. Singh et al., *Vaccine* 24 (2006) 1680-1686 and the references cited therein.

In some embodiments, the microparticles comprise one or more metabolizable oils. The metabolizable oil is commonly one having about 6 to about 30 carbon atoms including, but not limited to, alkanes, alkenes, alkynes, and their corresponding acids and alcohols, the ethers and esters thereof, and mixtures thereof. The oil can have a straight or branched chain structure. It can be fully saturated or have one or more double or triple bonds. Where mono or poly ester- or ether-based oils are employed, the limitation of about 6 to about 30 carbons applies to the individual fatty acid or fatty alcohol moieties, not the total carbon count. The oil can be essentially any vegetable oil, fish oil, animal oil or synthetically prepared oil which can be metabolized by the body of the host animal. For example, the oil component of this invention can be any long chain alkane, alkene or alkyne, or an acid or alcohol derivative thereof, for example, as the free acid, its salt or an ester thereof, such as a mono-, or di- or tri-esters, for instance, triglycerides, esters of 1,2-propanediol or similar poly-hydroxy alcohols. Alcohols can be acylated employing amino- or poly-functional acid, for example acetic acid, propanoic acid, citric acid or the like. Ethers derived from long chain alcohols which are oils and meet the criteria set forth herein can also be used.

As a specific example, many fish contain metabolizable oils which may be readily recovered. For instance, cod liver oil, shark liver oils, and whale oil such as spermaceti exemplify several of the fish oils, which may be used herein. A number of branched chain oils can be synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene. Fish oils, including squalene and squalane, the saturated analog to squalene, are readily available from commercial sources or may be obtained by methods known in the art. The metabolizable oil may be stabilized in the form of an emulsion using one or more suitable surfactants. The immunogenic emulsion compositions typically comprise (1) about 0.5 to 1 to 2 to 6 to 10 to 20% by volume oil, more typically 1 to 10% by volume oil, and even more typically 2 to 6% by volume oil, (2) about 80 to 90 to 95 to 98 to 99 to 99.5% by volume water, more typically 90 to 99% by volume water; and (3) an amount of one or more surfactants sufficient to stabilize the oil droplets (microparticles).

Preferably, substantially all of the oil droplets are smaller than 1 micron in diameter, more typically smaller than 250 nm. By "substantially all" is meant at least about 80% (by number), typically at least about 90%, more typically at least about 95% or even at least 98%. In order to produce such emulsions, a number of techniques can be used. For example, commercial emulsifiers can be used, which operate by the principle of high shear forces developed by forcing fluids through small apertures under high pressure. Examples of commercial emulsifiers include, without limitation, Model 110Y microfluidizer (Microfluidics, Newton, Mass.), Gaulin Model 30CD (Gaulin, Inc., Everett, Mass.), and Rainnie Minilab Type 8.30H (Miro Atomizer Food and Dairy, Inc., Hudson, Wis.). The appropriate pressure for use with an individual emulsion is readily determined by one of skill in the art. The size of the oil droplets can be varied, for example, by changing the ratio of surfactant to oil (increasing the ratio typically decreases droplet size), operating pressure (increasing operating pressure typically decreases droplet size) and operating temperature (increasing temperature typically decreases droplet size). Droplet size will also vary with the particular surfactant and oil used, as well as other components present, if any, at the time of emulsification (e.g., imidazoquinoline, antigen, and/or any optional supplemental compounds discussed below).

There are a number of surfactants specifically designed for and commonly used in biological situations. For example, a number of biological surfactants are listed as such by Sigma Chemical Company on pages 310-316 of its 1987 Catalog of Biochemical and Organic Compounds. Surfactants may be divided into four basic types: anionic, cationic, zwitterionic, and nonionic. Examples of anionic surfactants include alginic acid, caprylic acid, cholic acid, 1-decanesulfonic acid, deoxycholic acid, 1-dodecanesulfonic acid, sodium dodecyl sulfate (SDS), sodium lauryl sulfate (SLS), dioctyl sodium sulfosuccinate (DSS), N-lauroylsarcosine, and taurocholic acid, among others. Examples of cationic surfactants include dodecyltrimethylammonium bromide, cetyltrimethylammonium bromide or "CTAB" (e.g., cetrimide), dimethyl dioctodecyl ammonium bromide (DDA), dioleoyl-3-trimethylammonium-propane (DOTAP) benzalkonium chloride, benzyldimethylhexadecyl ammonium chloride, cetylpyridinium chloride, methylbenzethonium chloride, and 4-picoline dodecyl sulfate, among others. Examples of zwitterionic surfactants include 3-[(3-cholamidopropyl)-dimethylammonio]-1-propanesulfonate (commonly abbreviated CHAPS), 3-[(cholamidopropyl)dimethylammonio]-2-hydroxy-1-propanesulfonate (commonly abbreviated CHAPSO), N-dodecyl-N,N-dimethyl-3-ammonio-1-propanesulfonate, and lyso-alpha-phosphatidylcholine, among others. Examples of nonionic surfactants include polyvinyl alcohol (PVA), povidone (also known as polyvinylpyrrolidone or PVP), polysorbates, polyoxyethylated alkyl phenols, poloxamers, decanoyl-N-methylglucamide, diethylene glycol monopentyl ether, n-dodecyl beta-D-glucopyranoside, ethylene oxide condensates of fatty alcohols (e.g., those sold under the trade name Lubrol), polyoxyethylated glycol monoethers, polyoxyethylene ethers of fatty acids (particularly $C_{12}$-$C_{20}$ fatty acids), and sorbitan esters including polyoxyethylene sorbitan fatty acid esters (e.g., sold under the trade name Tween®) and sorbitan fatty acid esters (e.g., sold under the trade name Span®), among others.

In certain embodiments, the oil microparticles may be stabilized using one or more sorbitan derivatives, for example, selected sorbitan fatty acid monoesters, sorbitan fatty acid sesquiesters, sorbitan fatty acid triesters, polyoxyethylene sorbitan fatty acid monoesters and polyoxyethylene sorbitan fatty acid triesters. For example, the oil microparticles may be stabilized using a sorbitan ester (e.g., sorbitan trioleate) and a polyoxyethylene sorbitan ester (e.g., polyoxyethylene sorbitan monooleate).

One specific example of a surfactant-stabilized microparticle composition is MF59, which is an aqueous dispersion of oil microparticles containing 4-5% w/v squalene microparticles, stabilized with 0.25-0.5 w/v % polysorbate 80 (Tween 80), 0.5% w/v sorbitan trioleate (Span 85) and optionally various amounts of MTP-PE (e.g., 0-100 μg/dose). Another specific example of a surfactant-stabilized microparticle composition is SAF, containing 10% Squalane, 0.4% Tween 80, 5% pluronic-blocked polymer L121, and thr-MDP (see below). Yet another specific example of a surfactant-stabilized microparticle composition is Ribi adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox).

For further description of suitable microparticles for use herein and methods of forming them, see U.S. Pat. Nos. 6,086,901, 6,299,884 and 6,451,325 and International Publication No. WO 00/50006.

In some embodiments, the microparticles comprise one or more biodegradable polymers. Examples of biodegradable polymers include biodegradable polyesters, for instance, poly (α-hydroxy acids), polyhydroxyvaleric acid, and polycaprolactone, polydioxanones, polyorthoesters, polyanhydrides, and polycyanoacrylates (e.g., polyalkylcyanoacrylate or "PACA"). More typically, microparticles for use with the present invention are polymer microparticles derived from poly(α-hydroxy acids), for example, from a poly(lactide) ("PLA") or a copolymer of lactide and glycolide, such as a poly(L-lactide-co-glycolide) or poly(D,L-lactide-co-glycolide) ("PLG"). The polymer microparticles may be derived from any of various polymeric starting materials which have a variety of molecular weights and, in the case of the copolymers such as PLG, a variety of monomer ratios (e.g., lactide:glycolide), the selection of which will be largely a matter of choice, depending in part on the coadministered species and the rate of degradation desired. Lactide/glycolide molar ratio may range, for example, from 10:90 or less to 15:85 to 25:75 to 40:60 to 45:55 to 50:50 to 55:45 to 60:40 to 75:25 to 85:15 to 90:10 or more, whereas biodegradable polymer molecular weights may range, for example, from 5,000 or less to 10,000 to 20,000 to 40,000 to 50,000 to 70,000 to 100,000 to 200,000 Daltons, or more. For example, a 50:50 PLG polymer, containing 50% D,L-lactide and 50% glycolide, will provide a fast resorbing copolymer while 75:25 PLG degrades more slowly, and 85:15 and 90:10, even more slowly, due to the increased lactide component. Mixtures of microparticles with varying lactide:glycolide ratios may also find use herein in order to achieve the desired release kinetics. Degradation rate of the microparticles of the present invention can also be controlled by such factors as polymer molecular weight and polymer crystallinity.

PLG copolymers with varying lactide:glycolide ratios and molecular weights are readily available commercially from a number of sources including from Boehringer Ingelheim, Germany and Birmingham Polymers, Inc., Birmingham, Ala., USA. Some exemplary PLG copolymers include: (a) RG 502, a PLG having a 50:50 lactide/glycolide molar ratio and a molecular weight of approx. 12,000 Da; (b) RG 503, a PLG having a 50:50 lactide/glycolide molar ratio and a molecular weight of approx. 34,000 Da; (c) RG 504, a PLG having a 50:50 lactide/glycolide molar ratio and a molecular weight of approx. 48,000 Da, (d) RG 752, a PLG having a 75:25 lactide/glycolide molar ratio and a molecular weight of approx. 22,000 Da; (e) RG 755, a PLG having a 75:25 lactide/glycolide molar ratio and a molecular weight of approx. 68,000 Da; and (f) RG 502 H, a PLG having a lactide/glycolide copolymer ratio of 50/50, having a free carboxyl end group, and having a molecular weight of approx. 7800 Da. PLG polymers can also be synthesized by simple polycondensation of the lactic acid component using techniques well known in the art, such as described in Tabata et al., *J. Biomed. Mater. Res.* (1988) 22:837-858.

Polymer microparticles are prepared using any of several methods well known in the art. For example, in some embodiments, double emulsion/solvent evaporation techniques, such as those described in U.S. Pat. No. 3,523,907 and Ogawa et al., *Chem. Pharm. Bull.* (1988) 36:1095-1103, can be used herein to make the microparticles. These techniques involve the formation of a primary emulsion consisting of droplets of polymer solution, which is subsequently mixed with a continuous aqueous phase containing a particle stabilizer/surfactant. In other embodiments, microparticles can also be formed using spray-drying and coacervation as described in, e.g., Thomasin et al., *J. Controlled Release* (1996) 41:131; U.S. Pat. No. 2,800,457; Masters, K. (1976) *Spray Drying* 2nd Ed. Wiley, New York; air-suspension coating techniques, such as pan coating and Wurster coating, as described by Hall et al., (1980) *The Wurster Process in Controlled Release Technologies: Methods, Theory, and Applications* (A. F. Kydonieus, ed.), Vol. 2, pp. 133-154 CRC Press, Boca Raton, Fla. and Deasy, P. B., *Crit. Rev. Ther. Drug Carrier Syst.* (1988) S(2):99-139; and ionic gelation as described by, e.g., Lim et al., *Science* (1980) 210:908-910. Polymeric nanoparticles can also be formed using the solvent displacement method as described in PCT/US06/46212 filed Dec. 1, 2006.

In certain embodiments, a water-in-oil-in-water (w/o/w) solvent evaporation system can be used to form the microparticles, along the lines described by O'Hagan et al., *Vaccine* (1993) 11:965-969, PCT/US99/17308 (WO 00/06123) to O'Hagan et al. and Jeffery et al., Pharm. Res. (1993) 10:362. In general, a polymer of interest such as PLG is dissolved in an organic solvent, such as ethyl acetate, dimethylchloride (also called methylene chloride and dichloromethane), acetonitrile, acetone, chloroform, and the like. The polymer will typically be provided in about a 1-30%, more typically about a 2-15%, even more typically about a 3-10% and most typically, about a 4-8% solution, in organic solvent. The polymer solution is then combined with a first volume of aqueous solution and emulsified to form an o/w emulsion. The aqueous solution can be, for example, deionized water, normal saline, a buffered solution, for example, phosphate-buffered saline (PBS) or a sodium citrate/ethylenediaminetetraacetic acid (sodium citrate/ETDA) buffer solution. The latter solutions can (a) provide a tonicity, i.e., osmolality, that is essentially the same as normal physiological fluids and (b) maintain a pH compatible with normal physiological conditions. Alternatively, the tonicity and/or pH characteristics of the compositions of the present invention can be adjusted after microparticle formation and prior to administration. Preferably, the volume ratio of polymer solution to aqueous solution ranges from about 5:1 to about 20:1, more preferably about 10:1. Emulsification is conducted using any equipment appropriate for this task, and is typically a high-shear device such as, e.g., a homogenizer.

In some embodiments, one or more additional components are established within the microparticles. For example, antigen(s), imidazoquinoline(s) and/or the optional supplemental components described below can be introduced by adding the same (a) to the polymer solution, if in oil-soluble or oil-dispersible form or (b) to the aqueous solution, if in water-soluble or water-dispersible form.

A volume of the o/w emulsion is then combined with a larger second volume of an aqueous solution, which typically contains a surfactant. The volume ratio of aqueous solution to o/w emulsion typically ranges from about 2:1 to 10:1, more typically about 4:1. Examples of surfactants appropriate for the practice of the invention are listed above. Those of ordinary skill in the art may readily select surfactants appropriate for the type of species to be adsorbed. For example, microparticles manufactured in the presence of charged surfactants, such as anionic or cationic surfactants, may yield microparticles with a surface having a net negative or a net positive charge, which can adsorb a wide variety of molecules. For example, microparticles manufactured with anionic surfactants, such as sodium dodecyl sulfate (SDS), e.g., SDS-PLG microparticles, readily adsorb positively charged species, for example, polypeptide-containing species such as proteins. Similarly, microparticles manufactured with cationic surfactants, such as CTAB, e.g., CTAB-PLG microparticles, readily adsorb negatively charged species, for example, polynucleotide-containing species such as DNA. Certain species may adsorb more readily to microparticles having a combination of surfactants. Moreover, in some instances, it may be desirable to add surfactant to the above organic solution.

This mixture is then homogenized to produce a stable w/o/w double emulsion. Each of the above homogenization steps is typically conducted at a room temperature (i.e., 25° C.) or less, more typically less, for example, while cooling within an ice bath.

Organic solvent(s) is/are then evaporated. Following preparation, microparticles can be used as is or lyophilized for future use.

The formulation parameters can be manipulated to allow the preparation of small microparticles on the order of 0.05 μm (50 nm) to larger microparticles 50 μm or even larger. See, e.g., Jeffery et al., *Pharm. Res.* (1993) 10:362-368; McGee et al., *J. Microencap.* (1996). For example, reduced agitation typically results in larger microparticles, as do an increase in internal phase volume and an increase in polymer concentration. Small particles are typically produced by increased agitation as well as low aqueous phase volumes, high concentrations of emulsion stabilizers and a decrease in polymer concentration.

E. Antigens

Antigens useful in the present invention include, for example and without limitation, antigens derived from the herpesvirus family, including antigens derived from herpes simplex virus (HSV) types 1 and 2, such as HSV-1 and HSV-2 glycoproteins gB, gD and gH; antigens derived from varicella zoster virus (VZV), Epstein-Barr virus (EBV) and cytomegalovirus (CMV) including CMV gB and gH; and antigens derived from other human herpesviruses such as HHV6 and HHV7. (See, e.g. Chee et al., Cytomegaloviruses (J. K. McDougall, ed., Springer-Verlag 1990) pp. 125-169, for a review of the protein coding content of cytomegalovirus; McGeoch et al., J. Gen. Virol. (1988) 69:1531-1574, for a discussion of the various HSV-1 encoded proteins; U.S. Pat. No. 5,171,568 for a discussion of HSV-1 and HSV-2 gB and gD proteins and the genes encoding therefor; Baer et al., Nature (1984) 310:207-211, for the identification of protein coding sequences in an EBV genome; and Davison and Scott, J. Gen. Virol. (1986) 67:1759-1816, for a review of VZV.)

Antigens from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV), can also be conveniently used in the techniques described herein. By way of example, the viral genomic sequence of HCV is known, as are methods for obtaining the sequence. See, e.g., International Publication Nos. WO 89/04669; WO 90/11089; and WO 90/14436, incorporated by reference herein in their entireties. The HCV genome encodes several viral proteins, discussed further below. These proteins, as well as antigenic fragments thereof, will find use in the present invention. Similarly, the sequence for the .delta.-antigen from HDV is known (see, e.g., U.S. Pat. No. 5,378,814) and this sequence can also be conveniently used in the present invention. Additionally, antigens derived from HBV, such as the core antigen, the surface antigen, sAg, as well as the presurface sequences, pre-S1 and pre-S2 (formerly called pre-S), as well as combinations of the above, such as sAg/pre-S1, sAg/pre-S2, sAg/pre-S1/pre-S2, and pre-S1/pre-S2, will find use herein. See, e.g., "HBV Vaccines—from the laboratory to license: a case study" in Mackett, M. and Williamson, J. D., Human Vaccines and Vaccination, pp. 159-176, for a discussion of HBV structure; and U.S. Pat. Nos. 4,722,840, 5,098,704, 5,324,513, incorporated herein by reference in their entireties; Beames et al., J. Virol. (1995) 69:6833-6838, Birnbaum et al., J. Virol. (1990) 64:3319-3330; and Zhou et al., J. Virol. (1991) 65:5457-5464.

Antigens derived from other viruses will also find use in the invention, such as without limitation, antigens derived from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae (e.g., HTLV-I; HTLV-II; HIV-1 (also known as HTLV-III, LAV, ARV, hTLR, etc.)), including but not limited to antigens from the isolates $HIV_{IIIb}$, $HIV_{SF2}$, $HIV_{LAV}$, $HIV_{LAI}$, $HIV_{MN}$); $HIV-1_{CM235}$, $HIV-1_{US4}$; HIV-2; simian immunodeficiency virus (SIV) among others. Additionally, antigens may also be derived from human papillomavirus (HPV) and the tick-borne encephalitis viruses. See, e.g. Virology, 3rd Edition (W. K. Joklik ed. 1988); Fundamental Virology, 2nd Edition (B. N. Fields and D. M. Knipe, eds. 1991), for a description of these and other viruses.

More particularly, the gp120 envelope protein from any of the above HIV isolates, including members of the various genetic subtypes of HIV, are known and reported (see, e.g., Myers et al., Los Alamos Database, Los Alamos National Laboratory, Los Alamos, N. Mex. (1992); Myers et al., Human Retroviruses and Aids, 1990, Los Alamos, N. Mex.: Los Alamos National Laboratory; and Modrow et al., J. Virol. (1987) 61:570-578, for a comparison of the envelope gene sequences of a variety of HIV isolates) and sequences derived from any of these isolates will find use in the present methods. Furthermore, the invention is equally applicable to other immunogenic proteins derived from any of the various HIV isolates, including any of the various envelope proteins such as gp160, gp140 and gp41, gag antigens such as p24gag and p55gag, as well as proteins derived from the pol region.

Influenza virus is another example of a virus for which the present invention is useful. Specifically, antigens derived from influenza virus include the envelope glycoproteins HA and NA of influenza A, which are of particular interest for generating an immune response. Numerous HA subtypes of influenza A have been identified (Kawaoka et al., Virology (1990) 179:759-767; Webster et al., "Antigenic variation among type A influenza viruses," p. 127-168. In: P. Palese and D. W. Kingsbury (ed.), Genetics of influenza viruses. Springer-Verlag, New York). Thus, proteins derived from any of these isolates can also be used in the invention described herein.

Antigens for use in the compositions and methods described herein may also be derived from numerous bacterial antigens, such as those from organisms that cause diphtheria, cholera, tuberculosis, tetanus, pertussis, meningitis, and other pathogenic states, including, without limitation, Meningococcus A, B and C, *Hemophilus influenza* type B (HIB), and *Helicobacter pylori* (e.g., Cag, Vac, Nap, HopX, HopY, urease, etc.). Examples of parasitic antigens include those derived from organisms causing malaria and Lyme disease.

Furthermore, the compositions and methods described herein provide a means for treating a variety of malignant cancers. For example, the present invention can be used to mount both humoral and cell-mediated immune responses to particular proteins specific to the cancer in question, such as an activated oncogene, a fetal antigen, or an activation marker. Such tumor antigens include any of the various MAGEs (melanoma associated antigen E), including MAGE 1, 2, 3, 4, etc. (Boon, T. Scientific American (March 1993): 82-89); any of the various tyrosinases; MART 1 (melanoma antigen recognized by T cells), mutant ras; mutant p53; p97 melanoma antigen; CEA (carcinoembryonic antigen), among others.

It is readily apparent that the present invention can be used to raise antibodies to a large number of antigens for diagnostic and immunopurification purposes, as well as to prevent or treat a wide variety of diseases.

As explained above, the compositions and methods of the present invention may employ HCV antigens. The genome of the hepatitis C virus typically contains a single open reading frame of approximately 9,600 nucleotides, which is transcribed into a polyprotein. The full-length sequence of the polyprotein is disclosed in European Publication No. 388,232 and U.S. Pat. No. 6,150,087, incorporated herein by reference in their entireties. As shown in Table 1, An HCV polyprotein, upon cleavage, produces at least ten distinct products, in the order of $NH_2$-Core-E1-E2-p7-NS2-NS3-NS4a-NS4b-NS5a-NS5b-COOH. The core polypeptide occurs at positions 1-191, numbered relative to HCV-1 (see, Choo et al. (1991) Proc. Natl. Acad. Sci. USA 88:2451-2455, for the HCV-1 genome). This polypeptide is further processed to produce an HCV polypeptide with approximately amino acids 1-173. The envelope polypeptides, E1 and E2, occur at about positions 192-383 and 384-746, respectively. The P7 domain is found at about positions 747-809. NS2 is an integral membrane protein with proteolytic activity and is found at about positions 810-1026 of the polyprotein. NS2, either alone or in combination with NS3 (found at about positions 1027-1657), cleaves the NS2-NS3 sissle bond which in turn generates the NS3 N-terminus and releases a large polyprotein that includes both serine protease and RNA helicase activities. The NS3 protease, found at about positions 1027-1207, serves to process the remaining polyprotein. The helicase activity is found at about positions 1193-1657. Completion of polyprotein maturation is initiated by autocatalytic cleavage at the NS3-NS4a junction, catalyzed by the NS3 serine protease. Subsequent N53-mediated cleavages of the HCV polyprotein appear to involve recognition of polyprotein cleavage junctions by an NS3 molecule of another polypeptide. In these reactions, NS3 liberates an NS3 cofactor (NS4a, found about positions 1658-1711), two proteins (NS4b found at about positions 1712-1972, and NS5a found at about positions 1973-2420), and an RNA-dependent RNA polymerase (NS5b found at about positions 2421-3011).

Sequences for HCV polyprotein products, and immunogenic polypeptides derived therefrom, are known (see, e.g., U.S. Pat. No. 5,350,671, incorporated herein by reference in its entirety). For example, a number of general and specific immunogenic polypeptides, derived from the HCV polyprotein, have been described. See, e.g., Houghton et al., European Publ. Nos. 318,216 and 388,232; Choo et al. Science (1989) 244:359-362; Kuo et al. Science (1989) 244:362-364; Houghton et al. Hepatology (1991) 14:381-388; Chien et al. Proc. Natl. Acad. Sci. USA (1992) 89:10011-10015; Chien et al. J. Gastroent. Hepatol. (1993) 8:S33-39; Chien et al., International Publ. No. WO 93/00365; Chien, D. Y., International Publ. No. WO 94/01778. These publications provide an extensive background on HCV generally, as well as on the manufacture and uses of HCV polypeptide immunological reagents. For brevity, therefore, the disclosure of these publications is incorporated herein by reference.

Any desired antigenic HCV polypeptide can be utilized with the present invention, including, for example, the E1 and/or E2 envelope glycoproteins of HCV, as well as E1E2 complexes, associated either through non-covalent or covalent interactions Such complexes may be made up of immunogenic fragments of E1 and E2 which comprise epitopes. For example, fragments of E1 polypeptides can comprise from about 5 to nearly the full-length of the molecule, such as 6, 10, 25, 50, 75, 100, 125, 150, 175, 185 or more amino acids of an E1 polypeptide, or any integer between the stated numbers. Similarly, fragments of E2 polypeptides can comprise 6, 10, 25, 50, 75, 100, 150, 200, 250, 300, or 350 amino acids of an E2 polypeptide, or any integer between the stated numbers. The E1 and E2 polypeptides may be from the same or different HCV strains. For example, epitopes derived from, e.g., the hypervariable region of E2, such as a region spanning amino acids 384-410 or 390-410, can be included in the E2 polypeptide. A particularly effective E2 epitope to incorporate into the E2 sequence or E1E2 complexes is one which includes a consensus sequence derived from this region, such as the consensus sequence for amino acids 390-410 of the HCV type 1 genome. Additional epitopes of E1 and E2 are known and described in, e.g., Chien et al., International Publication No. WO 93/00365, incorporated by reference herein in its entirety.

Moreover, the E1 and E2 polypeptides may lack all or a portion of the membrane spanning domain. The membrane anchor sequence functions to associate the polypeptide to the endoplasmic reticulum. Normally, such polypeptides are capable of secretion into growth medium in which an organism expressing the protein is cultured. However, as described in International Publication No. WO 98/50556, such polypeptides may also be recovered intracellularly. Secretion into growth medium is readily determined using a number of detection techniques, including, e.g., polyacrylamide gel electrophoresis and the like, and immunological techniques such as immunoprecipitation assays as described in, e.g., International Publication No. WO 96/04301, published Feb. 15, 1996. With E1, generally polypeptides terminating with about amino acid position 370 and higher (based on the numbering of HCV1 E1) will be retained by the ER and hence not secreted into growth media. With E2, polypeptides terminating with about amino acid position 731 and higher (also based on the numbering of the HCV1 E2 sequence) will be retained by the ER and not secreted. (See, e.g., International Publication No. WO 96/04301, published Feb. 15, 1996). It should be noted that these amino acid positions are not absolute and may vary to some degree. Thus, the present invention contemplates the use of E1 and E2 polypeptides which retain the transmembrane binding domain, as well as polypeptides which lack all or a portion of the transmembrane binding domain, including E1 polypeptides terminating at about amino acids 369 and lower, and E2 polypeptides, terminating at about amino acids 730 and lower, are intended to be captured by the present invention. Furthermore, the C-terminal truncation can extend beyond the transmembrane spanning domain towards the N-terminus. Thus, for example, E1 truncations occurring at positions lower than, e.g., 360 and E2 truncations occurring at positions lower than, e.g., 715, are also encompassed by the present invention. All that is necessary is that the truncated E1 and E2 polypeptides remain functional for their intended purpose. However, particularly preferred truncated E1 constructs are those that do not extend beyond about amino acid 300. Most preferred are those terminating at position 360. Preferred truncated E2 constructs are those with C-terminal truncations that do not extend beyond about amino acid position 715. Particularly preferred E2 truncations are those molecules truncated after any of amino acids 715-730, such as 725. If truncated molecules are used, it is preferable to use E1 and E2 molecules that are both truncated.

E2 exists as multiple species (Spaete et al., Virol. (1992) 188:819-830; Selby et al., J. Virol. (1996) 70:5177-5182; Grakoui et al., J. Virol. (1993) 67:1385-1395; Tomei et al., J. Virol. (1993) 67:4017-4026) and clipping and proteolysis may occur at the N- and C-termini of the E1 and E2 polypeptides. Thus, an E2 polypeptide for use herein may comprise at least amino acids 405-661, e.g., 400, 401, 402 . . . to 661, such as 384-661, 384-715, 384-746, 384-749 or 384-809, or 384 to any C-terminus between 661-809, of an HCV polyprotein, numbered relative to the full-length HCV-1 polyprotein. Similarly, preferable E1 polypeptides for use herein can comprise amino acids 192-326, 192-330, 192-333, 192-360, 192-363, 192-383, or 192 to any C-terminus between 326-383, of an HCV polyprotein.

The E1 and E2 polypeptides and complexes thereof may also be present as asialoglycoproteins. Such asialoglycoproteins are produced by methods known in the art, such as by using cells in which terminal glycosylation is blocked. When these proteins are expressed in such cells and isolated by GNA lectin affinity chromatography, the E1 and E2 proteins aggregate spontaneously. Detailed methods for producing these E1E2 aggregates are described in, e.g., U.S. Pat. No. 6,074,852, incorporated herein by reference in its entirety. For example, E1E2 complexes are readily produced recombinantly, either as fusion proteins or by e.g., co-transfecting host cells with constructs encoding for the E1 and E2 polypeptides of interest. Co-transfection can be accomplished either in trans or cis, i.e., by using separate vectors or by using a single vector which bears both of the E1 and E2 genes. If done using a single vector, both genes can be driven by a single set of control elements or, alternatively, the genes can be present on the vector in individual expression cassettes, driven by individual control elements. Following expression, the E1 and E2 proteins will spontaneously associate. Alternatively, the complexes can be formed by mixing the individual proteins together which have been produced separately, either in purified or semi-purified form, or even by mixing culture media in which host cells expressing the proteins have been cultured, if the proteins are secreted. Finally, the E1E2 complexes of the present invention may be expressed as a fusion protein wherein the desired portion of E1 is fused to the desired portion of E2.

Moreover, the E1E2 complexes may be present as a heterogeneous mixture of molecules, due to clipping and proteolytic cleavage, as described above. Thus, a composition including E1E2 complexes may include multiple species of E1E2, such as E1E2 terminating at amino acid 746 ($E1E2_{746}$), E1E2 terminating at amino acid 809 ($E1E2_{809}$), or any of the other various E1 and E2 molecules described above, such as E2 molecules with N-terminal truncations of from 1-20 amino acids, such as E2 species beginning at amino acid 387, amino acid 402, amino acid 403, etc.

E1E2 complexes are readily produced recombinantly, either as fusion proteins or by e.g., co-transfecting host cells with constructs encoding for the E1 and E2 polypeptides of interest. Co-transfection can be accomplished either in trans or cis, i.e., by using separate vectors or by using a single vector which bears both of the E1 and E2 genes. If done using a single vector, both genes can be driven by a single set of control elements or, alternatively, the genes can be present on the vector in individual expression cassettes, driven by individual control elements. Following expression, the E1 and E2 proteins will spontaneously associate. Alternatively, the complexes can be formed by mixing the individual proteins together which have been produced separately, either in purified or semi-purified form, or even by mixing culture media in which host cells expressing the proteins, have been cultured, if the proteins are secreted. Finally, the E1E2 complexes of the present invention may be expressed as a fusion protein wherein the desired portion of E1 is fused to the desired portion of E2.

Methods for producing E1E2 complexes from full-length, truncated E1 and E2 proteins which are secreted into media, as well as intracellularly produced truncated proteins, are known in the art. For example, such complexes may be produced recombinantly, as described in U.S. Pat. No. 6,121,020; Ralston et al., J. Virol. (1993) 67:6753-6761, Grakoui et al., J. Virol. (1993) 67:1385-1395; and Lanford et al., Virology (1993) 197:225-235.

Other HCV polypeptides may also be used in the invention. For example, HCV polypeptides derived from the Core region, such as polypeptides derived from the region found between amino acids 1-191; amino acids 10-53; amino acids 10-45; amino acids 67-88; amino acids 86-100; 81-130; amino acids 121-135; amino acids 120-130; amino acids 121-170; and any of the Core epitopes identified in, e.g., Houghton et al., U.S. Pat. No. 5,350,671; Chien et al. Proc. Natl. Acad. Sci. USA (1992) 89:10011-10015; Chien et al. J. Gastroent. Hepatol. (1993) 8:S33-39; Chien et al., International Publ. No. WO 93/00365; Chien, D. Y., International Publ. No. WO 94/01778; and U.S. Pat. No. 6,150,087, the disclosures of which are incorporated herein by reference in their entireties, will find use with the subject compositions and methods.

Additionally, polypeptides derived from the nonstructural regions of the virus will also find use herein. The NS3/4a region of the HCV polyprotein has been described and the amino acid sequence and overall structure of the protein are disclosed in Yao et al. Structure (November 1999) 7:1353-1363. See, also, Dasmahapatra et al., U.S. Pat. No. 5,843,752, incorporated herein by reference in its entirety. As indicated above, either the native sequence or immunogenic analogs can be used in the subject formulations. Dasmahapatra et al., U.S. Pat. No. 5,843,752 and Zhang et al., U.S. Pat. No. 5,990,276, both describe analogs of NS3/4a and methods of making the same.

Moreover, polypeptides for use in the subject compositions and methods may be derived from the NS3 region of the HCV polyprotein. A number of such polypeptides are known, including, but not limited to polypeptides derived from the c33c and c100 regions, as well as fusion proteins comprising an NS3 epitope, such as c25. These and other NS3 polypeptides are useful in the present compositions and are known in the art and described in, e.g., Houghton et al, U.S. Pat. No. 5,350,671; Chien et al. Proc. Natl. Acad. Sci. USA (1992) 89:10011-10015; Chien et al. J. Gastroent. Hepatol. (1993) 8:S33-39; Chien et al., International Publ. No. WO 93/00365; Chien, D. Y., International Publ. No. WO 94/01778; and U.S. Pat. No. 6,150,087, the disclosures of which are incorporated herein by reference in their entireties.

Further, multiple epitope fusion antigens (termed "MEFAs"), as described in International Publ. No. WO 97/44469, may be used herein. Such MEFAs include multiple epitopes derived from two or more of the various viral regions. The epitopes are preferably from more than one HCV strain, thus providing the added ability to protect against multiple strains of HCV in a single vaccine.

It should be noted that for convenience, the various HCV regions are generally defined with respect to the amino acid number relative to the polyprotein encoded by the genome of HCV-1a, as described in Choo et al. (1991) Proc Natl Acad Sci USA 88:2451, with the initiator methionine being designated position 1. However, the antigens for use with the present invention are not limited to those derived from the HCV-1a sequence. Any strain or isolate of HCV can serve as the basis for providing antigenic sequences for use with the invention. In this regard, the corresponding regions in another HCV isolate can be readily determined by aligning sequences from the two isolates in a manner that brings the sequences into maximum alignment.

Various strains and isolates of HCV are known in the art, which differ from one another by changes in nucleotide and amino acid sequence. For example, isolate HCV J1.1 is described in Kubo et al (1989) Japan. Nucl. Acids Res. 17:10367-10372; Takeuchi et al. (1990) Gene 91:287-291; Takeuchi et al. (1990) J. Gen. Virol. 71:3027-3033; and Takeuchi et al. (1990) Nucl. Acids Res. 18:4626. The complete coding sequences of two independent isolates, HCV-J and BK, are described by Kato et al., (1990) Proc. Natl. Acad. Sci. USA 87:9524-9528 and Takamizawa et al., (1991) J. Virol. 65:1105-1113, respectively. HCV-1 isolates are described by Choo et al. (1990) Brit. Med. Bull. 46:423-441; Choo et al. (1991) Proc. Natl. Acad. Sci. USA 88:2451-2455 and Han et al. (1991) Proc. Natl. Acad. Sci. USA 88:1711-1715. HCV isolates HC-J1 and HC-J4 are described in Okamoto et al. (1991) Japan J. Exp. Med. 60:167-177. HCV isolates HCT 18.about, HCT 23, Th, HCT 27, EC1 and EC10 are described in Weiner et al. (1991) Virol. 180:842-848. HCV isolates Pt-1, HCV-K1 and HCV-K2 are described in Enomoto et al. (1990) Biochem. Biophys. Res. Commun. 170:1021-1025. HCV isolates A, C, D & E are described in Tsukiyama-Kohara et al. (1991) Virus Genes 5:243-254. HCV polypeptides for use in the compositions and methods of the invention can be obtained from any of the above cited strains of HCV or from newly discovered isolates isolated from tissues or fluids of infected patients.

Other antigens useful in the present invention are those derived from HIV. The HIV genome includes the regions known as Gag (p55gag), Pol, Vif, Vpr, Tat, Rev, Vpu, Env and/or Nef. HIV antigens from any of these regions, from any of the various subtypes, such as HIV subtype B and HIV subtype C, as well as any of the various isolates will find use with the present invention. It will be readily apparent to one of ordinary skill in the art in view of the teachings of the present disclosure how to determine corresponding regions in other HIV strains or variants (e.g., isolates $HIV_{IIIb}$, $HIV_{SF2}$, HIV-$1_{SF162}$, HIV-$1_{SF170}$, $HIV_{LAV}$, $HIV_{LAI}$, $HIV_{MN}$, HIV-$1_{CM235}$, HIV-$1_{US4}$, other HIV-1 strains from diverse subtypes (e.g., subtypes, A through G, and O), HIV-2 strains and diverse subtypes, and simian immunodeficiency virus (SIV). (See, e.g., Virology, 3rd Edition (W. K. Joklik ed. 1988); Fundamental Virology, 2nd Edition (B. N. Fields and D. M. Knipe, eds. 1991); Virology, 3rd Edition (Fields, B N, D M Knipe, P M Howley, Editors, 1996, Lippincott-Raven, Philadelphia, Pa.; for a description of these and other related viruses), using for example, sequence comparison programs (e.g., BLAST and others described herein) or identification and alignment of structural features (e.g., a program such as the "ALB" program described herein that can identify the various regions).

The envelope protein of HIV is a glycoprotein of about 160 kd (160). During virus infection of the host cell, gp160 is cleaved by host cell proteases to form gp120 and the integral membrane protein, gp41. The gp41 portion is anchored in the membrane bilayer of virion, while the gp120 segment protrudes into the surrounding environment. gp120 and gp41 are more covalently associated and free gp120 can be released from the surface of virions and infected cells. The gp120 polypeptide is instrumental in mediating entry into the host cell. Recent studies have indicated that binding of CD4 to gp120 induces a conformational change in Env that allows for binding to a co-receptor (e.g, a chemokine receptor) and subsequent entry of the virus into the cell. (Wyatt, R., et al. (1998) Nature 393:705-711; Kwong, P., et al. (1998) Nature 393:648-659). CD4 is bound into a depression formed at the interface of the outer domain, the inner domain and the bridging sheet of gp120.

Recombinant methods of obtaining the various HIV antigens once the region desired is identified are well known in the art. See, also, U.S. Pat. No. 5,614,612, incorporated herein by reference in its entirety.

Moreover, modified sequences of any of these HIV regions, such as modified gp120 and p55gag, can be used in the present invention. Sequences can be modified for optimum codon usage to simulate human codons and to reduce toxicity. Such modified sequences are known in the art and the sequences and methods of producing the same are described in detail in commonly owned International Publication Nos. WO 00/39304 and WO 00/39302, as well as in International Publication No. WO 98/34640, all incorporated herein by reference in their entireties.

The present invention is also useful for antigens derived from Neisseria spp., such as N. meningitidis, the causative agent of bacterial meningitis and sepsis. Meningococci are divided into serological groups based on the immunological characteristics of capsular and cell wall antigens. Currently recognized serogroups include A, B, C, W-135, X, Y, Z and 29E. For purposes of the present invention, a meningococcal antigen may be derived from any of the various known serogroups. The polysaccharides responsible for the serogroup specificity have been purified from several of these groups, including A, B, C, W-135 and Y. Effective capsular polysaccharide-based vaccines have been developed against meningococcal disease caused by serogroups A, C, Y and W135 and any of these vaccine antigens will find use in the present compositions and methods. See, e.g., International Publication Nos. WO 96/29412, WO 96/14086, WO 99/57280, WO 00/22430, WO 99/24578, WO 99/36544, as well as Tettelin et al. (2000) Science 287:1809-1815 and Pizza et al. (2000) Science 287:1816-1820, all incorporated by reference herein in their entireties, for a description of various meningococcal protein antigens that will find use herein. Additionally, saccharide antigens, such as those from N. meningitidis serogroup A, C W135 and/or Y, such as described in Costantino et al. (1992) Vaccine 10:691-698 and Costantino et al. (1999) Vaccine 17:1251-1263 will find use herein. Other useful Neisseria antigens include those derived from N. gonorrhoeae, for example, those described in International Publication Nos. WO 99/57280, WO 99/24578 and WO 99/36544.

For example, N. meningitidis serogroup B (termed "MenB" herein) accounts for a large percentage of bacterial meningitis in infants and children residing in the U.S. and Europe. Accordingly, antigens derived from MenB are particularly useful with the present compositions and methods, such as any of the antigens expressed by the various open reading frames (ORFs) of the MenB genome. See, e.g., International Publication No. WO 99/57280. Examples of such antigens include MenB proteins 961 and 287. Other meningococcal antigens for use herein include derivatives of the capsular MenB polysaccharide (termed "MenB PS derivatives" herein). Examples of MenB PS derivatives are described in EP Publication No. 504,202 B and U.S. Pat. No. 4,727,136. Also useful are molecular mimetics of unique epitopes of MenB PS as described in U.S. Pat. No. 6,030,619. Additionally, outer membrane vesicle preparations from MenB, such as those described in International Patent Application PCT/IB01/00166, Bjune et al. (1991) Lancet 338: 1093-1096, Fukasawa et al. (1999) Vaccine 17:2951-2958 and Rosenquist et al. (1998) Dev. Biol. Stand. 92:323-333. All of the above references are incorporated herein by reference in their entireties.

The complete genomic sequence of MenB, strain MC58, has been described. Tettelin et al., Science (2000) 287:1809. Several proteins that elicited serum bactericidal antibody responses have been identified by whole genome sequencing. Many of these proteins have sequences that are highly conserved among Neisseria meningitidis. Pizza et al., Science (2000) 287:1816. Accordingly, such antigens will find use in the present invention.

As noted above, in some embodiments, the antigen may be provided in the form protein particles as described in U.S. Pat. No. 6,534,064 to O'Hagan et al. and Pub. No. US 2005/0107322 to O'Hagan et al. Such particles may be formed from suitable antigens selected from those above, among others.

For example, in some embodiments, the antigen is a microparticle produced by a process comprising the steps of: (a) forming a particle from an aqueous solution; (b) stabilizing the antigen particle by a stabilizing treatment; and (c) recovering the antigen particle from the aqueous solution.

In some embodiments, the process of producing an antigen microparticle includes a solvent evaporation technique. Solvent evaporation techniques are known to those of skill in the art and described herein.

In some embodiments, the process of producing an antigen microparticle is based on the use of precipitation agents, for example, by adding a precipitation agent to an aqueous solution of an antigen and stirring the resulting mixture to form the particle. Examples of precipitation agents include, but are not limited to, one or more of oils, hydrocarbons or coacervation agents. In some embodiments, this process can further include an acid. Examples of acids include, but not limited to, acetic acid, glycolic acid, hydroxybutyric acid, hydrochloric acid or lactic acid.

A stabilizing treatment may be performed which can, for example, comprise one or more of heat treatment or treatment with a chemical cross-linking agent. Processes of heat treatment or chemical-cross linking are known. See, e.g., U.S. Pat. No. 6,534,064 to O'Hagan et al. or Pub. No. US 2005/0107322 to O'Hagan et al.

Combinations of antigens derived from the one or more organisms can be conveniently used to elicit immunity to multiple pathogens in a single vaccine. An example of antigens in a multiple pathogen vaccine is a combination of bacterial surface oligosaccharides derived from MenC and Hib, conjugated to a nontoxic mutant carrier derived from a bacterial toxin, such as a nontoxic mutant of diphtheria toxin known as $CRM_{197}$. This conjugate is useful for preventing bacterial meningitis and is described in International Publication No. WO 96/14086, published May 17, 1996.

F. Supplemental Components

The compositions of the present invention optionally include a variety of supplemental components. Such optional supplemental components include pharmaceutically acceptable excipients and supplementary immunological adjuvants, such as those described below, among others.

As noted above, where the microparticles are solid microparticles, optional supplemental components can be, for example: (a) established within the microparticles, for example, entrapped, encapsulated, dissolved or dispersed in the microparticles, including separate populations of microparticles, (b) attached to the microparticles, for example, adsorbed or conjugated to the surface of the microparticles, including separate populations of microparticles, or (c) otherwise associated with the microparticles to varying degrees, for example, admixed with the microparticles in a liquid dispersion, admixed with the microparticles in a solid composition (e.g., colyophilized with the microparticles), and so forth.

Where the microparticles are liquid microparticles (e.g., oil droplets in an oil-in-water emulsion, etc.), optional supplemental components may independently be, for example: dissolved or dispersed within the oil phase(s) of the emulsion (including separate populations of oil droplets), dissolved or dispersed within the aqueous phase of the emulsion and/or disposed at the interfaces between aqueous and oil phases of the emulsion.

Optional supplemental components include supplementary immunological adjuvants, which may be used to further enhance the effectiveness of the immunogenic compositions. For example, such immunological adjuvants may be administered concurrently with the immunogenic compositions of the present invention, e.g., in the same composition (e.g., as described in the preceding paragraphs) or in separate compositions. Such adjuvants may be administered prior or subsequent to the immunogenic compositions of the present invention.

Supplementary immunological adjuvants include, but are not limited to: (1) saponin adjuvants, such as Quil A, or QS21 (e.g., Stimulon (Cambridge Bioscience, Worcester, Mass.)) may be used or ISCOMs (immunostimulating complexes) generated therefrom, which ICOMS may be devoid of additional detergent e.g., WO00/07621; (2) Complete Freunds Adjuvant (CFA) and Incomplete Freunds Adjuvant (IFA); (3) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (4) phospholipid adjuvants, including lipopolysaccharide and liposaccharide phosphate adjuvants, for example, monophosphoryl lipid A (MPL), 3-O-deacylated MPL (3dMPL) e.g. GB-2220221, EP-A-0689454, optionally in the substantial absence of alum when used with pneumococcal saccharides e.g. WO00/56358; as well as aminoalkyl glucosamine phosphate compounds such as those described in U.S. Pat. No. 6,355,257 and phospholipids with linear alkane groups such as those described in Pub. No. US 2004/0202669; (5) immunostimulatory oligonucleotides including oligonucleotides comprising CpG motifs (Roman et al., *Nat. Med.,* 1997, 3, 849-854; Weiner et al., *PNAS USA,* 1997, 94, 10833-10837; Davis et al., *J. Immunol.* 1988, 160, 870-876; Chu et al., *J. Exp. Med.,* 1997, 186, 1623-1631; Lipford et al., *Eur. J. Immunol.* 1997, 27, 2340-2344; Moldoveanu et al., *Vaccine,* 1988, 16, 1216-1224, Krieg et al., *Nature,* 1995, 374, 546-549; Klinman et al., *PNAS USA,* 1996, 93, 2879-2883: Ballas et al., *J. Immunol.,* 1996, 157, 1840-1845; Cowdery et al., *J. Immunol.,* 1996, 156, 4570-4575; Halpern et al., *Cell. Immunol.,* 1996, 167, 72-78; Yamamoto et al., *Jpn. J. Cancer Res.,* 1988, 79, 866-873; Stacey et al., *J. Immunol,* 1996, 157, 2116-2122; Messina et al., *J. Immunol.,* 1991, 147, 1759-1764; Yi et al., *J. Immunol.,* 1996, 157, 4918-4925; Yi et al., *J. Immunol.,* 1996, 157, 5394-5402; Yi et al., *J. Immunol.,* 1998, 160, 4755-4761; and Yi et al., *J. Immunol.,* 1998, 160, 5898-5906; International patent applications WO96/02555, WO98/16247, WO98/18810, W098/40100, WO98/55495, WO98/37919 and WO98/52581) i.e. containing at least one CG dinucleotide (a cytosine nucleotide followed by a guanosine nucleotide), with 5 methylcytosine optionally being used in place of cytosine; (6) a polyoxyethylene ether or a polyoxyethylene ester e.g. WO99/52549; (7) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (8) a saponin and an immunostimulatory oligonucleotide (e.g., a CpG oligonucleotide) (WO00/62800); (9) a saponin and an oil-in-water emulsion e.g. WO99/11241; (10) a saponin (e.g. QS21)+3dMPL+IL-12 (optionally+a sterol) e.g. WO98/57659; (11) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO093/13202 and WO92/19265); (12) aminoalkyl glucosaminide 4-phosphates (AGP's), see, e.g., Johnson, D. A. et al.; Bioorg. Med. Chem. Lett., 1999 Aug. 2; 9(15):2273-8; (13) lipopolysaccharide mimetics (including monophosphoryl lipid A mimetics), such as non-saccharide phospholipids (e.g., simplified lipid A analogs lacking a disaccharide) described in Hawkins, L. D. et al; J. Pharmacol. Exp. Ther., 2002 February; 300(2):655-61 and U.S. Pat. No. 6,290,973; (14) adjuvants comprising natural or synthetic double-stranded RNA ("dsRNA"), which is generally made up of intermittent riboguanylic acid-ribocytidylic acid ([rG-rC]) and riboadenylic acid-polribouridylic acid ([rA-rU]) base pairs; for further information see, e.g., commonly owned PCT/US02/30423; (15) muramyl peptides such as N-acetyl-muramyl-L-threonyl-D-isoglutamine (thr-MDP), N-acteyl-normuramyl-L-alanyl-D-isogluatme (nor-MDP), N-acetyl-muramyl-L-alanyl-D-isogluatminyl-L-alanine-2-(1'-2'-dipalmitoyl-sn-glycero-3-huydroxyphosphoryloxy)-ethylamine (MTP-PE), etc; (16) thiosemicarbazone compounds such as those described in WO 04/60308; (17) tryptanthrin compounds such as those described in WO 04/64759; (18) polyphosphazene (PCPP) formulations such as those described, for example, in Andrianov et al. (1998) *Biomaterials* 19(1-3):109-115 and Payne et al. (1998) *Adv. Drug Del. Rev.* 31(3):185-196; (19) Lipid A Derivatives including derivatives of lipid A from *Escherichia coli* such as OM-174, described for example in Meraldi et al. (2003) *Vaccine* 21:2485-2491 and Pajak et al. (2003) *Vaccine* 21:836-842; and (20) other substances that act as immunostimulating agents to enhance the effectiveness of the composition.

For additional examples of adjuvants, see *Vaccine Design, The Subunit and the Adjuvant Approach,* Powell, M. F. and Newman, M. J, eds., Plenum Press, 1995).

G. Formulation and Administration

As noted above, the antigen(s), imidazoquinoline(s) or various supplementary components of the compositions of the invention may be established within (e.g., entrapped, encapsulated, dissolved or dispersed) the solid or liquid microparticles, for example, by introducing these species during the microparticle manufacturing process. The antigen(s), imidazoquinoline(s) or various supplementary components may also be attached to the microparticles (e.g., conjugated or adsorbed) or otherwise associated with the microparticles, for example, by introducing these species to previously microparticle formation. Adsorption and other associations may be established by simply admixing these species and the microparticles. Conjugation of such species to microparticles may be based on various linking chemistries known in the art including carbodiimide coupling and solubility profiles. In some embodiments, the antigen(s), imidazoquinoline(s) or various supplementary components are otherwise associated with the microparticles to varying degrees, for example, by admixing them with the microparticles in a liquid dispersion, admixing them with the microparticles in a solid composition (e.g., colyophilized with the microparticles), and so forth.

The compositions of the present invention will commonly include one or more pharmaceutically acceptable excipients. For example, pharmaceutically acceptable vehicles such as water, saline, glycerol, ethanol, etc. may be used. Other excipients, such as wetting or emulsifying agents, osmotic agents, biological buffering substances, and the like, may be present. A biological buffer can be virtually any solution which is pharmacologically acceptable and which provides the formulation with the desired pH, i.e., a pH in the physiological range. Examples include phosphate buffers, citrate buffers, borate buffers, succinate buffers, and histidine buffers, as well as saline buffer combinations, including phosphate buffered saline, Tris buffered saline, Hank's buffered saline, and the like. Examples of osmotic agents include salts, sugars, etc.

Depending on the final dosage form, other excipients known in the art can also be introduced, including binders, disintegrants, fillers (diluents), lubricants, glidants (flow enhancers), compression aids, preservatives, suspensing/dispersing agents, film formers/coatings, and so forth.

Once formulated, the compositions of the invention can be administered parenterally, e.g., by injection. The compositions can be injected either subcutaneously, intraperitoneally, intravenously or intramuscularly. Other modes of administration include oral and pulmonary administration, suppositories, mucosal and transdermal applications. Dosage treatment may be a single dose schedule or a multiple dose schedule. A multiple dose schedule is one in which a primary course of vaccination may be with 1-10 separate doses, followed by other doses given at subsequent time intervals, chosen to maintain and/or reinforce the immune response, for example at 1-4 months for a second dose, and if needed, a subsequent dose(s) after several months. The dosage regimen will also, at least in part, be determined by the need of the subject and be dependent on the judgment of the practitioner. Furthermore, if prevention of disease is desired, the vaccines are generally administered prior to primary infection with the pathogen of interest or prior to the advent of tumor cells. If therapeutic treatment is desired, the vaccines are generally administered subsequent to primary infection or appearance of tumor cells.

In some embodiments, the compositions of the present invention can be used for site-specific targeted delivery. For example, intravenous administration of the compositions can be used for targeting the lung, liver, spleen, blood circulation, or bone marrow.

EXAMPLES

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Formulation Preparation

Materials for this Example are as follows: (1) RG503 PLG, having a lactide/glycolide copolymer ratio of 50/50, obtained from Boehringer Ingelheim, USA, (2) RG 502 H PLG, having a lactide/glycolide copolymer ratio of 50/50 and having a free carboxyl end group, obtained from Boehringer Ingelheim, USA, (3) dioctyl sulfosuccinate (DSS) obtained from Sigma Chemicals, St. Louis, Mo., USA, (4) imidazoquinoline 090 (synthesis described in Int. Pub. Nos. WO 2006/031878 to Valiante et al. and WO 2007/109810 to Sutton et al.).

Anionic PLG microparticles with encapsulated imidazoquinoline 090 were prepared using a solvent evaporation technique. Briefly, the microparticles were prepared by emulsifying 4 mL of a 15% w/v polymer solution (RG503 or RG502H) in methylene chloride with 1.0 mL of PBS 1× at high speed using an IKA homogenizer. Imidazoquinoline 090 was dispersed in the oil phase before emulsification and was used in the microparticle formulation in an amount equal to 1% w/w relative to PLG. The primary emulsion was then added to 32 mL of distilled water containing DSS (0.5% w/w) and homogenized using an Omni homogenizer. This resulted in the formation of a w/o/w emulsion, which was stirred for 12 h at room temperature, allowing the methylene chloride to evaporate.

Formulations were formed by adsorbing antigen to the above PLG microparticles with encapsulated imidazoquinoline 090. The antigen, Men B 287 protein, was adsorbed to the particles in an amount of 1% w/w PLG on a lab rocker overnight at 4 deg C. Sugars (mannitol at 4.5% and sucrose at 1.5% of the reconstitution volume) were added and aliquots of the formulation were then placed into small glass vials and lyophilized.

Lyophilized antigen adsorbed PLG microparticles were formed by the following procedure: Anionic PLG microparticles were prepared using a solvent evaporation technique. Briefly, the microparticles were prepared by emulsifying 4 mL of a 6% w/v polymer solution (RG503) in methylene chloride with 1.0 mL of PBS 1× at high speed using an IKA homogenizer. The primary emulsion was then added to 32 mL of distilled water containing DSS (0.05% w/w) and homogenized using an Omni homogenizer. This resulted in the formation of a w/o/w emulsion, which was stirred for 12 h at room temperature, allowing the methylene chloride to evaporate. Formulations were formed by adsorbing the antigen, Men B 287, to the above anionic PLG microparticles in an amount of 1% w/w PLG on a lab rocker overnight at 4 deg C. Sugars (mannitol at 4.5% and sucrose at 1.5% of the reconstitution volume) were added and aliquots of the formulation were then placed into small glass vials and lyophilized.

A soluble imidazoquinoline 090 formulation was formed by adding an imidazoquinoline 090 solution (100 µg/ml) to reconstituted lyophilized antigen adsorbed PLG microparticles in accordance with the prior paragraph. The soluble imidazoquinoline 090 was added in an amount of 10% w/w PLG. Antigen dose was 1 µg.

A colyophilized imidazoquinoline 090 formulation was formed by adsorbing Men B 287 protein antigen in an amount of 1% w/w PLG on imidazoquinoline 090 adsorbed PLG microparticles on a lab rocker overnight at 4 deg C. Imidazoquinoline 090 adsorbed PLG microparticles were formed by adsorbing imidazoquinoline 090 on anionic PLG microparticles, formed as above, by adding a solution of imidazoquinoline 090 (100 ug/ml) to PLG microparticles (10% w/w PLG for groups containing 1 µg antigen) and adsorption was carried out overnight on a lab rocker at 4 deg C. Sugars (mannitol at 4.5% and sucrose at 1.5% of the reconstitution volume) were added and aliquots of the formulation were then placed into small glass vials and lyophilized.

Example 2

In vitro Release Profile

In vitro release was measured by the following procedure: Vials of each of the above imidazoquinoline-090-containing formulations were kept on a rocker at room temperature (after reconstituting the lyophilized formulations in water). Samples were collected at time 0, 7 days, 14 days, 28 days and 42 days and centrifuged. Imidazoquinoline 090 was measured in the supernatant by RP-HPLC.

Figure 1:
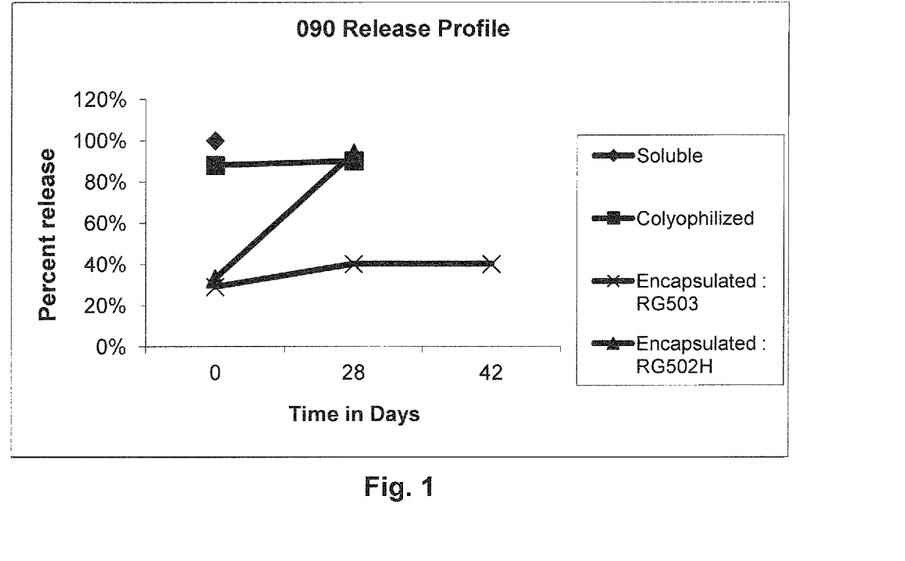
FIG. 1 shows imidazoquinoline 090 release as a function of time from four different formulations.

The results are shown in FIG. 1. As can be seen from FIG. 1, the soluble formulation had an immediate release of imidazoquinoline 090, the release from the colyophilized imidazoquinoline 090 formulation was essentially immediate, the encapsulated imidazoquinoline 090 (using RG502H) was essentially all released by 28 days, and a substantial amount of the encapsulated imidazoquinoline 090 (using RG503) remained unreleased, even after 42 days.

Example 3

In Vivo Study

For group 1 "PLG/287" in Table 1 below, PLG/287 vials containing 0.1 mg of PLG and 1 µg adsorbed 287 antigen per animal prepared as in Example 1 were reconstituted with Water for Injection at the time of immunization.

For group 2 "PLG/287+soluble 090" in Table 1 below, vials containing Men B 287 (1 µg 287 adsorbed on 0.1 mg of PLG per animal prepared as in Example 1) were reconstituted with Water for Injection and soluble imidazoquinoline 090 was added (10 µg per animal) at the time of immunization.

For group 3 "PLG/Colyophilized 090/287" in Table 1 below, vials containing PLG (0.1 mg per animal) with colyophilized adsorbed imidazoquinoline 090 (10 µg per animal) and adsorbed Men B 287 (1 µg per animal) prepared as in Example 1 were reconstituted with Water for Injection at the time of immunization.

For group 4 "RG503 PLG/090 Encapsulated/287" in Table 1 below, vials containing PLG RG 503 (0.1 mg per animal), encapsulated imidazoquinoline 090 (10 µg per animal) and adsorbed Men B 287 (1 µg per animal) prepared as in Example 1 were reconstituted with Water for Injection at the time of immunization.

For group 4 "RG502H/090 Encapsulated/287" in Table 1 below, vials of containing PLG RG 502H (0.1 mg per animal), encapsulated imidazoquinoline 090 (10 µg per animal) and adsorbed Men B 287 (1 µg per animal) prepared as in Example 1 were reconstituted with Water for Injection at the time of immunization.

For all groups, samples were injected IM into groups of 10 female CD-1 mice on day(s) 0, 21 and 35. At day 39 and day 56, serum ELISA titers were analyzed as described in Singh, M. et al. (2004) *J. Pharm. Sci.* 93(2):273-282, and at day 56 serum bactericidal activity (SBA) was analyzed as described in Pizza, M. et al. (2000) *Science* 287(5459): 1816-1820. 2996 is the strain of MenB used for SBA analysis.

The results are presented in Table 1 below. As seen from the table, entrapment of imidazoquinoline 090 in RG 503 PLG (Group 4), enhanced antibody titers (IgG), by approximately two-fold and serum bactericidal titers (SBA) by four-fold when compared to adsorbed Men B 287 alone (Group 1) and adsorbed Men B 287 with soluble imidazoquinoline 090 (Group 2). The entrapment of imidazoquinoline 090 in RG 502H PLG (Group 5) was more comparable to adsorbed Men B 287 alone (Group 1) and adsorbed Men B 287 with soluble imidazoquinoline 090 (Group 2). The colyophilised formulation (Group 3) was comparable to adsorbed Men B 287 alone (Group 1) and adsorbed Men B 287 with soluble imidazoquinoline 090 (Group 2), although SBA titers were reduced.

TABLE 1

IgG and SBA titers.

| Group | Formulation | 2wp3 IgG GMT | 2wp3 SBA 2996 |
|---|---|---|---|
| 1 | PLG/287 | 9,341 | 256 |
| 2 | PLG/287 + soluble 090 | 6,323 | 256 |
| 3 | PLG/Colyophilized 090/287 | 6,729 | 128 |
| 4 | RG503 PLG/090 Encapsulated/287 | 15,724 | 1024 |
| 5 | RG502H/090 Encapsulated/287 | 11,390 | 256 |

Thus, novel compositions and methods for using and making the same are disclosed. While the present invention has been described with reference to the specific embodiments thereof, it should be understood by those skilled in the art that various changes may be made and equivalents may be substituted without departing from the true spirit and scope of the invention.

We claim:

1. An immunogenic composition comprising (a) a first antigen, (b) at least first and second adjuvants, wherein the first adjuvant comprises an organic microparticle and wherein the second adjuvant comprises an imidazoquinoline compound that is established within said microparticle, and (c) a pharmaceutically acceptable excipient, wherein said composition elicits an immune response against said first antigen when administered to a vertebrate subject.

2. The immunogenic composition of claim 1, wherein the first adjuvant comprises at least 50 wt % (dry basis) of the composition.

3. The immunogenic composition of claim 1, wherein said microparticle comprises a biodegradable polymer.

4. The immunogenic composition of claim 3, wherein said biodegradable polymer is a polyhydroxy acid.

5. The immunogenic composition of claim 3, wherein said biodegradable polymer comprises a poly(α-hydroxy acid) that is selected from poly(lactide), poly(glycolide), poly(lactide-co-glycolide) and combinations thereof.

6. The immunogenic composition of claim 3, wherein the microparticle further comprises a surfactant selected from an anionic surfactant, a cationic surfactant, a zwitterionic surfactant, and a nonionic surfactant.

7. The immunogenic composition claim 3, wherein the microparticle is formed by a precipitation process.

8. The immunogenic composition claim 3, wherein the microparticle is formed by a solvent evaporation process.

9. The immunogenic composition of claim 1, wherein said microparticle comprises L-tyrosine.

10. The immunogenic composition of claim 1, wherein said microparticle comprises a metabolizable oil.

11. The immunogenic composition of claim 10, wherein said metabolizable oil is a terpenoid.

12. The immunogenic composition of claim 10, wherein said metabolizable oil is squalene.

13. The immunogenic composition of claim 1, wherein the first adjuvant is MF59.

14. The immunogenic composition of claim 1, wherein the second adjuvant comprises from 5% w/w to 20% w/w relative to the material forming the microparticle.

15. The immunogenic composition of claim 1, wherein the first antigen comprises from 0.5% w/w to 10.0% w/w relative to the material forming the microparticle.

16. The immunogenic composition of claim 1, wherein said first antigen is established within said microparticle.

17. The immunogenic composition of claim 1, wherein said first antigen is adsorbed to said microparticle.

18. The immunogenic composition of claim 1, wherein the first antigen is admixed with said microparticle.

19. The immunogenic composition of claim 1, wherein the first antigen comprises a polypeptide-containing antigen.

20. The immunogenic composition of claim 1, wherein the first antigen comprises a polysaccharide-containing antigen.

21. The immunogenic composition of claim 1, wherein the first antigen comprises a conjugate antigen.

22. The immunogenic composition of claim 1, wherein the first antigen comprises a polynucleotide-containing antigen.

23. The immunogenic composition of claim 1, wherein the first antigen is a microparticle.

24. The immunogenic composition of claim 1, wherein first antigen is a tumor-cell antigen.

25. The immunogenic composition of claim 1, wherein the first antigen is a pathogenic-organism antigen.

26. The immunogenic composition of claim 25, wherein the pathogenic organism is selected from a virus, a bacterium, a fungus and a parasite.

27. The immunogenic composition of claim 26, wherein the pathogenic organism is selected from hepatitis virus, varicella, poliovirus, measles, mumps, rubella, influenza virus, *Neisseria meningitidis*, pertussis, *Haemophilus influenzae* type b, HIV, herpes simplex virus type 2, pertussis, diphtheria, tetanus, *H. pylori*, and *Streptococcus pneumoniae*.

28. The immunogenic composition of claim 26, wherein the pathogenic organism is selected from HIV, hepatitis B virus, hepatitis C virus, meningitis B, *Haemophilus influenza* type b and influenza A virus.

29. The immunogenic composition of claim 1, wherein the antigen comprises a killed or attenuated pathogenic organism.

30. The immunogenic composition of claim 1, further comprising a third adjuvant distinct from the first and second adjuvants.

31. The immunogenic composition of claim 1, further comprising a second antigen distinct from the first antigen.

32. The immunogenic composition of claim 1, wherein the immunogenic composition is an injectable composition.

33. The immunogenic composition of claim 1, wherein the composition elicits a cellular immune response in a vertebrate subject and wherein the first antigen is from an entity selected from the group consisting of a tumor, a virus, a bacterium, a fungus, and a parasite.

34. The immunogenic composition of claim 33, wherein the vertebrate subject is a human.

35. The immunogenic composition of claim 33 wherein the cellular immune response is a cytotoxic-T lymphocyte (CTL) response.

36. A method of producing a microparticle composition in accordance with claim 3 comprising: (a) providing an emulsion comprising water, organic solvent, said biodegradable polymer and said second adjuvant, (b) removing the organic solvent from the emulsion to form microparticles, and (c) adding the first antigen, wherein the first antigen is added to the emulsion or added to the microparticles after they are formed, and wherein the first antigen is adsorbed on, established within or admixed with said microparticles.

37. The method of claim 36, wherein said emulsion comprises the first antigen.

38. The method of claim 36, wherein the first antigen is adsorbed to said microparticles.

39. A method of forming a microparticle composition comprising a first antigen, an imidazoquinoline compound, and microparticles comprising a biodegradable polymer, said method comprising: (a) emulsifying an organic phase comprising the biodegradable polymer, the imidazoquinoline and an organic solvent with a first aqueous phase comprising water, thereby forming a water-in-oil emulsion; (b) emulsifying a second aqueous phase comprising water with the emulsion formed in step (a) to form a water-in-oil-in-water emulsion; (c) removing the organic solvent from the water-in-oil-in-water emulsion to form microparticles, and (d) adding the first antigen, wherein the first antigen is added to the first aqueous phase or added to the microparticles after they are formed, and wherein the first antigen is adsorbed on, established within or admixed with the microparticles.

40. The method of claim 39, wherein said first aqueous phase comprises the first antigen.

41. The method of claim 39, wherein the first antigen is adsorbed to said microparticles.

42. The method of claim 39, wherein the second aqueous phase further comprises a surfactant.

43. The method of claim 42, wherein the surfactant is an anionic surfactant.

44. A method of raising an immune response in a vertebrate subject comprising administering the immunogenic composition of claim 1 to said vertebrate subject.

45. The method of claim 44, wherein the immunogenic composition is administered by a route of intramuscular, intratracheal, intranasal, transdermal, intradermal, subcutaneous, intraocular, vaginal, rectal, intraperitoneal, intraintestinal or inhalation administration.

46. The method of claim 45, wherein the first antigen is from a pathogenic organism selected from hepatitis virus, varicella, poliovirus, measles, mumps, rubella, influenza virus, *Neisseria meningitidis*, pertussis, *Haemophilus influenzae* type b, HIV, herpes simplex virus type 2, pertussis, diphtheria, tetanus, *H. pylori*, and *Streptococcus pneumoniae*.

47. A kit for preparing an immunogenic composition of claim 1, comprising a first container comprising said first antigen, a second container comprising said first adjuvant, said second adjuvant, and said excipient.

48. An immunogenic composition comprising (a) a first antigen, (b) at least first and second adjuvants, wherein the first adjuvant comprises a microparticle that comprises a biodegradable polymer, wherein the second adjuvant comprises an imidazoquinoline compound, wherein the second adjuvant is established within the microparticle, and wherein the first antigen is adsorbed to the microparticle, and (c) a pharmaceutically acceptable excipient, wherein said composition elicits an immune response against said first antigen when administered to a vertebrate subject.

49. The immunogenic composition of claim 48, wherein said microparticle comprises poly(lactide-co-glycolide).

50. The immunogenic composition of claim 49, wherein the microparticle further comprises an anionic surfactant.

51. The immunogenic composition of claim 50, wherein the first antigen comprises a polypeptide-containing antigen.

52. The immunogenic composition of claim 51, wherein the first antigen is a pathogenic-organism antigen.

53. The immunogenic composition of claim 51, wherein the first antigen is from *Neisseria meningitidis*.

54. The immunogenic composition of claim 51, wherein the first antigen is Men B 287 protein.

55. The immunogenic composition of claim 1, wherein said imidazoquinoline compound is imidazoquinoline 090, 56. The method of claim 39, wherein said imidazoquinoline compound is imidazoquinoline 090,

57. The immunogenic composition of claim 48, wherein said imidazoquinoline compound is imidazoquinoline 090,

\* \* \* \* \*